United States Patent [19]

Flanagan et al.

[11] Patent Number: 5,601,801
[45] Date of Patent: Feb. 11, 1997

[54] RADIOLABELLED ANGIOTENSIN CONVERTING ENZYME INHIBITORS

[75] Inventors: Richard J. Flanagan, St. Lazare; Duncan H. Hunter, London; Vincenzo Quiquero, Mississauga; Pamela Zabel, St. Mary's, all of Canada

[73] Assignee: Merck Frosst Canada, Inc., Kirkland, Canada

[21] Appl. No.: 284,767

[22] Filed: Aug. 2, 1994

[51] Int. Cl.$^6$ .......................... A61K 51/04; A01N 43/42; C07D 417/00; C07D 257/04

[52] U.S. Cl. .................. 424/1.85; 514/300; 514/312; 514/340; 514/252; 514/218; 514/384; 514/383; 544/60; 548/537

[58] Field of Search .......................... 424/1.85; 514/312, 514/300, 340, 252, 218, 384, 383; 260/112.5; 544/60; 548/250

[56] References Cited

U.S. PATENT DOCUMENTS

| | | | |
|---|---|---|---|
| 4,374,829 | 2/1983 | Harris et al. | 424/177 |
| 4,555,502 | 11/1985 | Patchett et al. | 514/19 |
| 4,574,079 | 3/1986 | Gavras et al. | 424/1.85 |
| 5,284,849 | 2/1994 | Rosenberg et al. | 514/252 |

FOREIGN PATENT DOCUMENTS 0012401  6/1980  European Pat. Off. .

OTHER PUBLICATIONS

Grönhagen–Riska et al., "Competitive inhibitor binding assay (CIBA) of captopril and other ACE inhibitors.", Clinica Chimica Acta, 53–60 pp., 162, (1987).

Hwang et al., J. Nucl. Med. 32(9), Sep. 1991, pp. 1730–1737.

*Primary Examiner*—Gary E. Hollinden
*Assistant Examiner*—Michael G. Hartley
*Attorney, Agent, or Firm*—J. Eric Thies; David L. Rose

[57] ABSTRACT

Angiotensin convening enzyme (ACE) inhibitors can be labelled with Iodine-123, Iodine-125, Iodine-127 or Iodine-131, useful to image the kidneys and lungs for diagnosis and treatment of diseases such as essential hypertension, renal artery stenosis, or diabetes which are associated with a change in the amount of ACE present in the human body.

3 Claims, No Drawings

RADIOLABELLED ANGIOTENSIN CONVERTING ENZYME INHIBITORS

BACKGROUND OF THE INVENTION

The renin-angiotensin system is one of the complicated mechanisms involved in blood pressure regulation. Renin, an enzyme produced in kidney, acts on the circulating protein angiotensinogen, produced in liver, to give a decapeptide, angiotensin I. Angiotensin I has no biologic activity and is the target of the angiotensin-converting enzyme (ACE), which is present in large quantities in lung.

ACE is a zinc ion mediated peptidyldipeptide hydrolase (EC 3.4.15.1). It catalyzes conversion of the inactive decapeptide angiotensin I to the potent vasocontrictor octapeptide angiotensin II, which also stimulates the release of aldosterone from the adrenal glands and leads to the sodium and water retention. ACE also catalyzes the inactivation of the naturally occurring vasodepressor bradykinin. The importance of these reactions in hypertensive disease has been clarified by the development of potent and specific inhibitors of ACE, e.g., lisinopril, elonapril, fosinopril and captopril. At present ACE inhibitors are an important class of therapeutic drags in treating hypertension.

The distribution, biotransformation, and excretion of the different ACE inhibitor drugs in animals has been studied with radiolabelled compounds. From these studies, it has been concluded that the kidney and liver show high levels of ACE inhibitor drugs, due to the excretory role of these organs; but that high amounts are also concentrated in lung tissue. The radiolabelling of the ACE inhibitor compounds, therefore, is a powerful tool to image those organs, in order to diagnose diseases such as essential hypertension, renal artery stenosis or diabetic nephropathy.

Positron-labelled ACE inhibitors (captopril) have been described, Hwang et al, *J. Nucl. Med.* 32 (9), September 1991, pp 1730–1737, and used to probe ACE activity in vivo by positron emission toniography (PET), but PET scanners are not as widely available as SPECT (single proton emission computed tomography) scanning technology. Thus, a need exists for radiolabelled ACE inhibitors as a diagnostic tool available in all nuclear medicine departments.

SUMMARY OF THE INVENTION

The present invention provides a method for radiolabelling the ACE inhibitor drug lysinobril using various radiohalogen isotopes, and the products so produced, useful to diagnosis and monitor the many diseases associated in a change in the amount of ACE present in the body. The use of I-123, I-125, I-127 or I-131 to form these radiolabelled compounds allow the readily available SPECT methodology to be used in the radioimaging studies, which allows tomography to be carried out with simple rotating head and cameras.

DETAILED DESCRIPTION OF THE INVENTION

The present invention provides the compound a radiolabelled derivative of lisinopril having the following structure

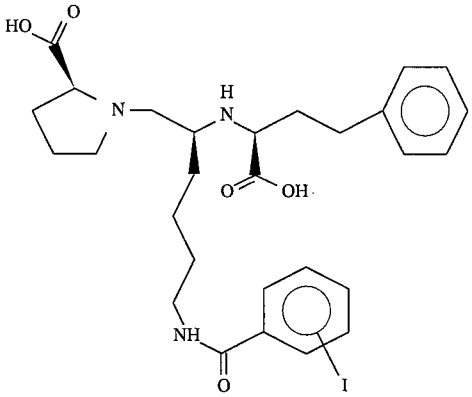

wherein I is I-125, I-123, or I-131 and is on the 2, 3, or 4 position of the phenyl ring.

The lisinopril derivatives are those described in EPO 0012401, published Jun. 25, 1980, and in U.S. Pat. Nos. 4,374,829, issued Feb. 22, 1983; and U.S. Pat. No. 4,555,502, issued Nov. 26, 1985.

The methodology for making the desirable radioiodinated ACE inhibitors utilizes as starting materials 3- or 4-iodobenzoic acid, which is reacted with approximately equinolar amounts of N-hydroxyl succinimide and DCC (1,3-dicyclohexyl-carbodiimide) in tetrahydrofuran or a suitable solvent such as dioxane or dimethoxyethane to give the N-hydroxysuccinimidyl 3-iodobenzoate intermediate as a precipitate, which can be purified. This intermediate is then transformed into the desired radioiodo isotope form using synthesis through a 3-tri-n-butylstannylbenzoate intermediate, which is a modification of a procedure published in *Int. J. Radiat. Appl. Instrum.* Part A, 38 (12) 1051 (1987), resulting in the desired radioiodo derivative, N-hydroxy succinimidyl 3-radioiodobenzoate. This compound is then reacted with the desired ACE inhibitor at the N-terminal amide group to form the desired N-radioiodobenzoamide compound.

The preferred radioiodine isotope is I-131, but any of the others: I-123, I-125, or I-127 can also be employed.

The uses to which the radioiodine ACE inhibitor can be put are in scanning and imaging the kidney and lungs for diagnostic purposes. The compound can be injected as a phosphate buffered saline solution and the patient imaged using a gamma camera. The best dosages are 1–5 mCi for 4 hr imaging times.

This invention is illustrated by the following examples.

EXAMPLE 1

N-Hydroxysuccinimidyl 3-iodobenzoate

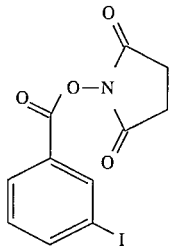

To a stirred solution of 3-iodobenzoic acid (1.0 g, 4.0 mmol) in 10 mL of anhydrous THF was added 1.2 equivalents each of DCC (1.0 g, 4.8 mmol) and N-hydroxysuccinimide (557 mg, 4.8 mmol). Stirring was continued for 16 hours at which point the resulting precipitate was filtered and the THF was removed in vacuo. The resulting solid, recrystallized from dichloromethane/diethyl ether, gave white crystals, mp 146°–148° C.; yield 695 mg, 70%.

$^1$HMR (CDCl$_3$) δ: 2.9 (s, 4H, CH$_2$), 7.2 (t, 1H, CH, J=8 Hz), 8.0 (d, 1H, CH, J=8 Hz), 8.1 (d, 1H, CH, J=8 Hz), 8.5 (s, 1H, CH). $^{13}$CMR (CDCl$_3$) δ: 25.5 (CH$_2$), 93.9 (CI), 126.9 (C), 129.6 (CH), 130.4 (CH), 139.1 (CH), 143.7 (CH), 160.5 (CO), 169.0 (CO).

M/e calculated for C$_{11}$H$_8$INO$_4$ 344.950. Found: (m/s) 344.950

EXAMPLE 2

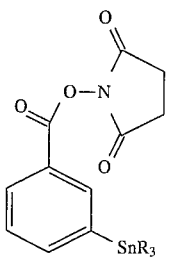

N-Hydroxysuccinimidyl 3-tri-n-butylstannylbenzoate (1)

This preparation is an improvement of the published procedure of Zalutsky et al., *Int. J. Radiat. Appl. Instrum.* 38, 1051, 1987. Zalutsky's method calls for a two step synthesis with purification by flash chromatography after each step. It was found that both purifications were labour intensive and often repetitive chromatography was needed to isolate the products. Adapting the procedure to a one pot synthesis decreased the time needed for purification.

A solution of 0.5 g of 3-iodobenzoic acid (2 mmol) in 10 mL of anhydrous THF in a 100 mL round bottom flask, under argon, was cooled to −98° C. in a liquid nitrogen-methanol bath. To this stirred solution was added 2.2 mL of 1.8M n-butyllithium in hexane (4 mmol) over a 15 minute period. When addition was complete, the resulting mixture was allowed to stir for an additional 15 minutes at which time a solution of 1.44 g of tri-n-butyl tin chloride (4.4 mmol) in 5 mL of anhydrous THF was added. The reaction was allowed to warm to −78° C. (methanol-dry ice) and stirred for 30 minutes and then allowed to warm to room temperature and stirred for 1.5 hours. A solution of 20 mL dry THF containing 0.62 g of DCC (3 mmol) and 0.35 g of N-hydroxysuccinimide was added to the mixture. The solution was stirred for 18 hours at room temperature at which time the gelatinous precipitate was filtered and washed with THF. Removal of the THF in vacuo was followed by repeated (3 times) flash chromatography over silica gel eluted with 10:1 hexanes:ethyl acetate. This gave 287 mg, 30% of (1) as a pale yellow oil. The observed spectra were identical to those reported in the literature.

$^1$HMR (CDCl$_3$) δ: 0.8–1.7 (m, 27H, 3×n-butyl), 2.9 (s, 4H, CH$_2$), 7.4 (t, 1H, CH, J=7 Hz), 7.8 (d, 1H, CH, J=7 Hz), 8.1 (d, 1H, CH, J=7 Hz), 8.2 (s, 1H, CH). $^{13}$CMR (CDCl$_3$) δ: 9.7 (C, CH$_2$), 13.7 (C, CH$_3$), 25.7 (C, CH$_2$), 27.3 (C, CH$_2$), 28.9 (C, CH$_2$), 29.0 (C, CH$_2$), 124.4 (C, C), 128.1 (C, CH), 130.1 (C, CH), 138.2 (C, CH), 143.0 (C, CH), 143.6 (C, C), 162.4 (C, CO), 169.4 (C, CO).

EXAMPLE 3

N-Hydroxysuccinimidyl 3-radioiodobenzoate (2)

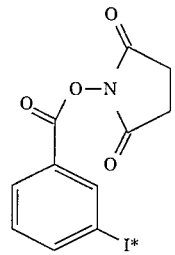

To 456 μCi (25 μL) of a Na$^{131}$I solution in a 1 mL V-shaped vial was added 0.5 mg of 1, 50 μL CH$_3$CN, an iodobead and a magnetic stir bar. The mixture was stirred for 30 minutes at which time the solution was drawn up into a 100 μL syringe. The vial was rinsed with 25 μL of CH$_3$CN and this was also drawn up into the syringe. This solution was purified by HPLC (250 mm RP-Select B, 50:50 CH$_3$CN:H$_2$O) and the peak corresponding to 2 was collected. This fraction was extracted with 2×1 mL of CHCl$_3$, the organic layers were combined and the CHCl$_3$ was evaporated in a stream of argon. This gave 347 μCi of 2.

EXAMPLE 4

Lisinopril N$^ε$-radioiodobezamide (3)

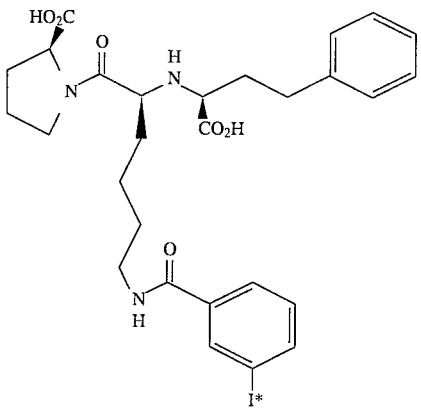

Compound 2 prepared as described above was taken up in 75 μL of 0.01M borax buffer (pH 8.3) containing 0.5 mg lisinopril. The mixture was stirred at room temperature for 3 hours at which time the solution was taken up in a 100 μL syringe. The vial was rinsed with 25 μL of borax buffer and this was also taken up in the syringe. The solution was purified by HPLC (250 mm RP-Select B, 30:70 $CH_3CN$: 0.005M tetrabutylammonium phosphate pH 7.7). The radioactive peak corresponding to 3 was collected and the solvent was taken off in a stream of argon to give 63 μCi of 3.

EXAMPLE 5

$IC_{50}$ Assay

According to the assay of Cushman and Cheung *Biochem. Pharmacol* 20, 1637, (1971), a slurry of 10 g of lyophilized rabbit lung powder (Pel-Freez) and 100 mL of 50 mM potassium phosphate buffer, pH 8.3, was blended for three one minute intervals followed by centrifugation for 40 minutes at 17,500 rpm. The clear supernatant was assayed for protein by the modified Lowry test and the volume of the rabbit lung powder extract (RLPE) was adjusted with buffer, 100 mM phosphate buffer prepared to yield a pH of 8.3 in the presence of 300 mM NaCl, to give 10–20 mU of angiotensin converting enzyme (ACE) activity in a 100 μL volume. The assay was carried out in 13×100 mm disposable culture tubes, with each assay tube containing 100 μL RLPE, 50 μL of a 12.5 mM solution of hippuryl-L-histidyl-L-leucine (HHL) (Sigma) in a buffer and 100 μL of inhibitor solution made up in buffer. The enzyme is added last to initiate the reaction and the tubes are incubated at 37° C. for one hour. The assay is terminated by the addition of 250 μL of 1M HCl to each tube; the HCl is added before the enzyme in the zero-time control assays. To each tube is added 1.5 mL of ethyl acetate followed by vortex mixing for 15 seconds. After the tubes have been centrifuged at 2,500 rpm for 5 minutes, 1 mL of the ethyl acetate layer is transferred to a clean 12×75 mm disposable culture tube. The ethyl acetate was evaporated by heating at 90° C. in a water bath for 30 minutes. Addition of 1 mL of water to each tube followed by vortex mixing for 15 seconds redissolves the hippuric acid. Measurement of the UV absorbance at 228 nm gave the date shown in Table 1. This gives an $IC_{50}$ for lisinopril of $5.4 \times 10^{-9}$ ($\pm 1 \times 10^{-9}$) M and for lisinopril MIBA of $6 \times 10^{-10}$ ($\pm 1 \times 10^{-1}$) M.

TABLE 1

| Absorbance readings from $IC_{50}$ assay | | | |
|---|---|---|---|
| −log[Lisin] | $A_{228} \pm SD$ | −log[MIBA] | $A_{228} \pm SD$ |
| 6.206 | 0.029 ± 0.007 | 7.246 | 0.025 ± 0.007 |
| 7.206 | 0.175 ± 0.007 | 8.246 | 0.224 ± 0.016 |
| 8.206 | 0.946 ± 0.012 | 9.246 | 1.196 ± 0.026 |
| 9.206 | 2.275 ± 0.031 | 10.246 | 2.174 ± 0.047 |
| 10.206 | 2.371 ± 0.060 | 11.246 | 2.360 ± 0.060 |

EXAMPLE 6

Biodistribution of $^{131}$I-3 in CD-1 Mice

It is well known that there are high ACE concentrations in the lungs, kidneys, pre-optic region of the brain and the blood.[4] Localization of the radioactivity in these organs was expected. Biodistribution results showed uptake in the kidneys and lungs at early time points with rapid clearance from the lungs. High uptake in the small intestine was also observed. This small intestine uptake was completely unexpected and had quite slow clearance. A blocking study was undertaken to differentiate between specific and non-specific binding.

$^{131}$I-3 was prepared as described above and used in this experiment. The experiment was carried out using male CD-1 mice. The mice were fasted 15 hours prior to injection with 1 μCi of $^{131}$I-3 by bolus injection into the lateral tail vein. At various times following the dosing, selected mice were sacrificed, exsanguinated and dissected. The desired organs were rinsed, blotted, weighed and counted. For the blocking experiment, mice were treated with 10 μg of lisinopril (by bolus injection into the lateral tail vein) 5 minutes before injection of $^{131}$I-3. The results of this biodistribution as shown in Table 2.

This blocking experiment was an attempt to differentiate between specific and non-specific binding. Non-specific binding would be demonstrated of the radiopharmaceutical bound in the presence of lisinopril. The data shows that the uptake in the kidney and small intestine is effectively blocked at all time points by pre-injection with an ACE inhibitor. This is illustrated by the dramatic decrease in radioactivity present in these organs in the blocked biodistribution as compared to the normal biodistribution. The kidney shows what appears to be a slight increase (or no change) at 0.5 hours and then we see blockage for all of the later time points. The anomaly of the first time point has yet to be explained. All of the other organs show no difference in uptake between the normal and blocked biodistributions. This data shown that the uptake in the kidney, lung and small intestine is due to specific binding.

EXAMPLE 7

Imaging of a New Zealand White Rabbit with $^{131}$I-3

An imaging study was undertaken in an attempt to explain the high uptake in the small intestine of mice. It was thought that this small intestine uptake could be due to a difference in mouse ACE or in its distribution as compared to human ACE. It was decided to carry out this imaging experiment in a rabbit since rabbit ACE is believed to be similar to human ACE. It should be noted that it was rabbit ACE which was used in the $IC_{50}$ assay.

TABLE 2

| Biodistribution of $^{131}$I-3 in CD-1 mice The data below represents percent injected dose per gram of tissue. | | | | | | | | |
|---|---|---|---|---|---|---|---|---|
| | Time (hours) | | | | | | | |
| | 0.5 | | 1.5 | | 3.0 | | 6.0 | |
| Organ | NB* | B** | NB* | B** | NB* | B** | NB* | B** |
| Kidney | 7.1 | 9.8 | 7.1 | 2.4 | 6.9 | 1.4 | 9.6 | 0.5 |
| Lung | 4.8 | 1.0 | 1.8 | 0.6 | 1.7 | 0.5 | 0.5 | 0.3 |
| Blood | 5.9 | 6.0 | 3.2 | 3.2 | 3.1 | 1.3 | 1.0 | 0.9 |
| Liver | 7.2 | 7.6 | 4.9 | 1.4 | 3.8 | 1.9 | 0.8 | 0.3 |

TABLE 2-continued

Biodistribution of $^{131}$I-3 in CD-1 mice
The data below represents percent injected dose per gram of tissue.

| Organ | Time (hours) | | | | | | | |
|---|---|---|---|---|---|---|---|---|
| | 0.5 | | 1.5 | | 3.0 | | 6.0 | |
| | NB* | B** | NB* | B** | NB* | B** | NB* | B** |
| Muscle | 1.1 | 1.1 | 0.8 | 0.4 | 0.6 | 0.3 | 0.3 | 0.2 |
| Fat | 0.7 | 0.6 | 0.8 | 0.5 | 0.4 | 0.2 | 0.2 | 0.1 |
| Sm. Intest. | 31.9 | 19.8 | 27.0 | 21.7 | 27.0 | 14.2 | 20.1 | 1.2 |
| lg. Intest. | 1.5 | 1.1 | 1.1 | 1.4 | 2.6 | 13.4 | 18.6 | 14.6 |
| Stomach | 25.1 | 24.2 | 28.7 | 13.3 | 14.2 | 12.8 | 5.1 | 4.2 |
| Contents | 21.4 | 17.9 | 22.1 | 28.5 | 21.4 | 15.0 | 65.9 | 48.9 |

*Normal (not blocked) biodistrubtion.
**Blocked biodistrubtion.

$^{131}$I-3 prepared as described above was taken up in phosphate buffered saline, the solution was filtered through a 0.2μ Millipore filter, and was introduced into the rabbit by intravenous ear injection followed by imaging of the rabbit. Pictures taken clearly show the lungs and kidneys at early time points, as well as in the bladder at later time points.

What is claimed is:

1. A compound which is $N^{\alpha}$-((S)-1-carboxy-3-phenylpropyl-$N^{\epsilon}$-3-iodo-benzoyl-L-lysyl-L-proline, wherein iodo is selected from $^{127}$I, $^{123}$I, $^{125}$I, and $^{131}$I.

2. A compound having the structure:

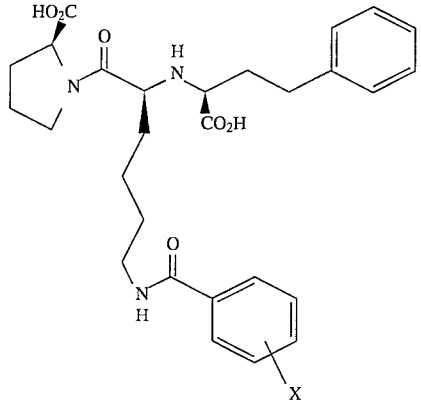

wherein X is selected from $^{127}$I, $^{123}$I, $^{125}$I, and $^{131}$I, and is located at the 2-, 3- or 4-position.

3. The compound of claim 2 wherein X is $^{131}$I, and is located at the 3-position.

* * * * *